United States Patent
Fiss Hobart et al.

(10) Patent No.: US 12,385,101 B2
(45) Date of Patent: Aug. 12, 2025

(54) **COMPOSITIONS AND METHODS FOR DETECTION OF *NEISSERIA GONORROHEAE***

(71) Applicant: Roche Molecular Systems, Inc., Pleasanton, CA (US)

(72) Inventors: Ellen H. Fiss Hobart, Albany, CA (US); Jingtao Sun, San Ramon, CA (US)

(73) Assignee: Roche Molecular Systems, Inc., Pleasanton, CA (US)

(*) Notice: Subject to any disclaimer, the term of this patent is extended or adjusted under 35 U.S.C. 154(b) by 951 days.

(21) Appl. No.: 17/609,124

(22) PCT Filed: May 5, 2020

(86) PCT No.: PCT/EP2020/062367
§ 371 (c)(1),
(2) Date: Nov. 5, 2021

(87) PCT Pub. No.: WO2020/225231
PCT Pub. Date: Nov. 12, 2020

(65) Prior Publication Data
US 2022/0220539 A1    Jul. 14, 2022

Related U.S. Application Data

(60) Provisional application No. 62/844,569, filed on May 7, 2019.

(51) Int. Cl.
*C12Q 1/689* (2018.01)
*C12Q 1/6818* (2018.01)

(52) U.S. Cl.
CPC ........... *C12Q 1/689* (2013.01); *C12Q 1/6818* (2013.01)

(58) Field of Classification Search
None
See application file for complete search history.

(56) References Cited

U.S. PATENT DOCUMENTS

| | | | | |
|---|---|---|---|---|
| 5,962,273 A * | 10/1999 | Durmowicz | ........... | C12Q 1/689 435/6.15 |
| 7,476,736 B2 | 1/2009 | Kawa et al. | | |
| 7,790,386 B2 * | 9/2010 | Ku | ........... | C12Q 1/689 435/6.15 |

FOREIGN PATENT DOCUMENTS

| | | |
|---|---|---|
| EP | 1586663 A1 | 10/2005 |
| EP | 1847616 B1 | 9/2011 |
| JP | 2009533023 A | 9/2009 |
| WO | 2016086305 A1 | 6/2016 |

OTHER PUBLICATIONS

Marangoni et al. Evaluation of the new test VERSANT CT/GC DNA 1.0 assay for the detection of Chlamydia trachomatis and Neisseria gonorrhoeae in urine specimens. J Clin Lab Anal. Feb. 2012;26(2):70-2. doi: 10.1002/jcla.21485. PMID: 22467321; PMCID: PMC6807475 (Year: 2012).*
Black, L.W., "Old, new and widely true: The bacteriophage T4 packaging mechanism", Virology, 2015, 479-480, p. 650-656.
Marri, P.R. et al., "Genome Sequencing Reveals Widespread Virulence Gene Exchange among Human Neisseria Species", PLOS One, Jul. 2010, vol. 5, Issue 7, e11835, p. 1-9.
International Search Report and Written Opinion for PCT/EP2020/062367, mailed Jul. 10, 2020.

* cited by examiner

Primary Examiner — Aaron A Priest
Assistant Examiner — Tian Nmn Yu
(74) Attorney, Agent, or Firm — Daniel E. Agnew

(57) ABSTRACT

Methods for the rapid detection of the presence or absence of NG Pilin Inverting protein ($Piv_{Ng}$) gene in a biological or non-biological sample are described. The methods can include performing an amplifying step, a hybridizing step, and a detecting step. Furthermore, primers, probes targeting the NG $Piv_{Ng}$ genes, along with kits are provided that are designed for the detection of *Neisseria gonorrhoeae* (NG).

8 Claims, 1 Drawing Sheet
Specification includes a Sequence Listing.

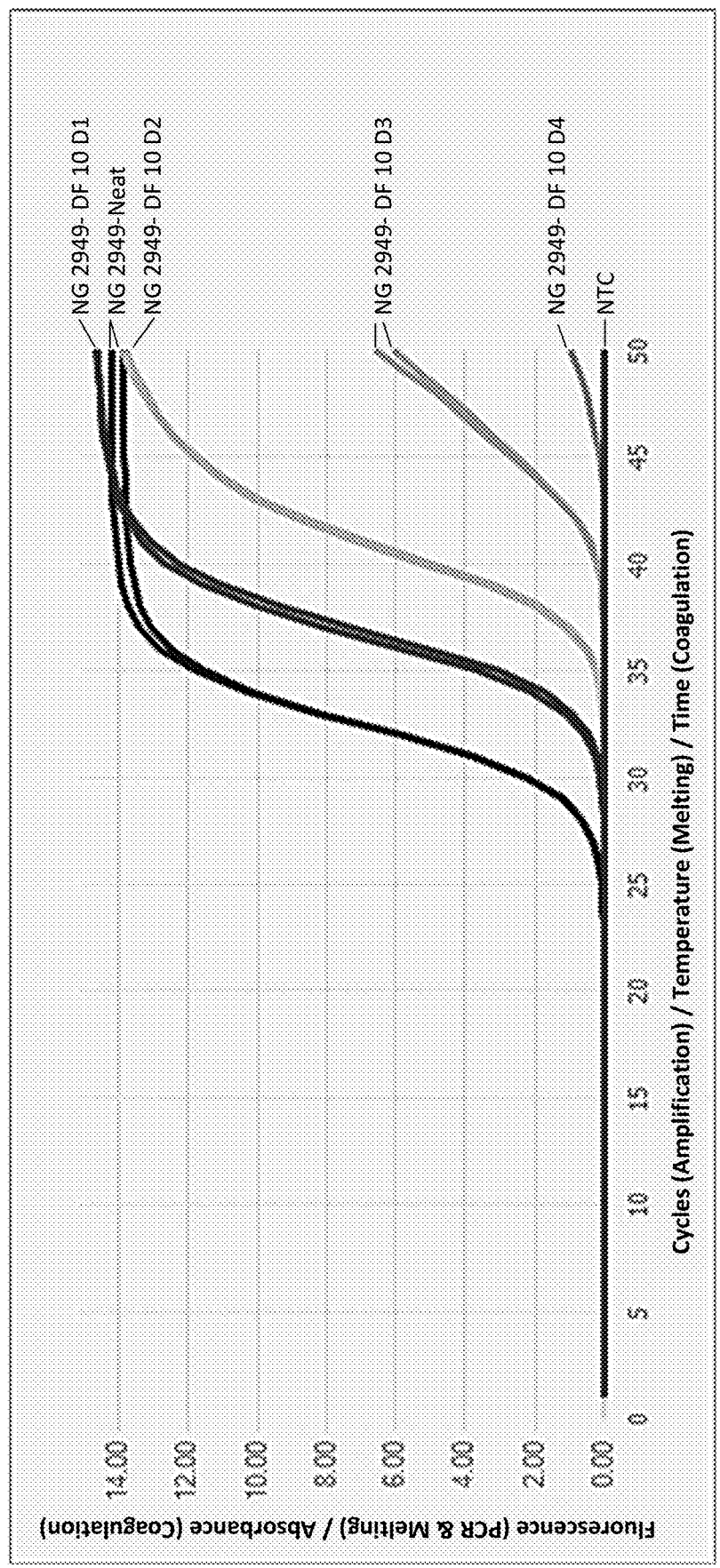

COMPOSITIONS AND METHODS FOR DETECTION OF *NEISSERIA GONORROHEAE*

CROSS REFERENCE TO RELATED APPLICATIONS

This application is a U.S. national stage filing under 35 U.S.C. § 371 of International Application No. PCT/EP2020/062367, filed May 5, 2020, entitled "COMPOSITIONS AND METHODS FOR DETECTION OF *NEISSERIA GONORROHEAE*", which claims the benefit of priority to U.S. Provisional Patent Application No. 62/844,569, filed on May 7, 2019, each of which is hereby incorporated in its entirety by reference.

FIELD OF THE INVENTION

The present disclosure relates to the field of molecular diagnostics, and more particularly to detection of *Neisseria gonorroheae*.

REFERENCE TO SEQUENCE LISTING

This application contains a Sequence Listing submitted as an electronic text file named "35265 US ST25.txt", having a size in bytes of 4 kb, and created on Apr. 7, 2020.

BACKGROUND OF THE INVENTION

*Neisseria gonorrhoeae* (NG), also known as gonococcus, or gonococci is a species of Gram-negative diplococci bacteria isolated by Albert Neisser in 1879. NG is the etiologic agent of gonorrhea and is a cytochrome oxidase-positive, non-motile, non-spore forming gram-negative diplococci. It causes the sexually transmitted genitourinary infection gonorrhea as well as other forms of gonococcal disease including disseminated gonococcemia, septic arthritis, and gonococcal ophthalmia neonatorum. *N. gonorrhoeae* infects the mucous membranes of the reproductive tract, including the cervix, uterus, and fallopian tubes in women, and the urethra in women and men. *N. gonorrhoeae* can also infect the mucous membranes of the mouth, throat, eyes, and rectum.

Gonorrhea is a very common infectious disease. CDC estimates that approximately 820,000 new gonococcal infections occur in the United States each year, and more than half of these infections are detected and reported to Center for Disease Control and Prevention (CDC). CDC estimates that 570,000 of them were among young people 15-24 years of age. In 2017, 555,608 cases of gonorrhea were reported to CDC.

Gonorrhea is transmitted through sexual contact with the penis, vagina, mouth, or anus of an infected partner. Ejaculation does not have to occur for gonorrhea to be transmitted or acquired.

Gonorrhea can also be spread perinatally from mother to baby during childbirth. People who have had gonorrhea and received treatment may be reinfected if they have sexual contact with a person infected with gonorrhea.

Gonorrhea is the second most commonly reported communicable disease. Clinical manifestations of NG infections are numerous. Many men with gonorrhea are asymptomatic. When present, signs and symptoms of urethral infection in men include dysuria or a white, yellow, or green urethral discharge that usually appears one to fourteen days after infection. In cases where urethral infection is complicated by epididymitis, men with gonorrhea may also complain of testicular or scrotal pain. In women, the primary site of infection is the endocervix. There is a high prevalence of coalescence of symptoms with *Chlamydia trachomatis* (CT), *Trichomonas vaginalis*, and vaginosis; many women remain asymptomatic and therefore do not seek medical care. Even when a woman has symptoms, they are often so mild and nonspecific that they are mistaken for a bladder or vaginal infection. The initial symptoms and signs in women include dysuria, increased vaginal discharge, or vaginal bleeding between periods. Women with gonorrhea are at risk of developing serious complications from the infection, regardless of the presence or severity of symptoms.

Other gonococcal infected sites in men and women are the pharynx, conjunctiva, and to a lesser degree the disease presents itself as disseminated gonococcal infection. Pharyngeal infection may cause a sore throat, but usually is asymptomatic. Infants from infected mothers can develop conjunctivitis.

Annual screening for *N. gonorrhoeae* infection is recommended for all sexually active women aged <25 years and for older women at increased risk for infection (e.g., those who have a new sex partner, more than one sex partner, a sex partner with concurrent partners, or a sex partner who has a sexually transmitted infection (STI).

If left untreated, gonorrhea can also spread to the blood and cause disseminated gonococcal infection (DGI). DGI is usually characterized by arthritis, tenosynovitis, and/or dermatitis. This condition can be life threatening. Untreated gonorrhea can increase a person's risk of acquiring or transmitting HIV, the virus that causes AIDS.

Urogenital gonorrhea can be diagnosed by testing urine, urethral (for men), or endocervical or vaginal (for women) specimens using nucleic acid amplification testing (NAAT). Therefore, there is a need in the art for a better and complete method to specifically detect NG.

SUMMARY OF THE INVENTION

Certain embodiments in the present disclosure relate to methods for the rapid detection of the presence or absence of NG in a biological or non-biological sample, for example, multiplex detection of NG by real-time polymerase chain reaction in a single test tube. Embodiments include methods of detection of NG comprising performing at least one cycling step, which may include an amplifying step and a hybridizing step. Furthermore, embodiments include primers, probes, and kits that are designed for the detection of NG in a single tube. The detection methods are designed to target specific genes in the *Neisseria gonorrhoeae* genome with a potential to discriminate against the other *Neisseria* species.

A method for detecting *Neisseria gonorrhoeae* (NG) in a sample is provided, including performing an amplifying step including contacting the sample with a set of primers designed to target a specific NG gene to produce an amplification product if NG is present in the sample; performing a hybridizing step including contacting the amplification product with one or more detectable probes to the target NG gene; and detecting the presence or absence of the amplified product, wherein the presence of the amplified product is indicative of the presence of NG in the sample and wherein the absence of the amplified product is indicative of the absence of NG in the sample; wherein the target NG gene is the Pilin Inverting protein ($Piv_{Ng}$) gene.

In one aspect a method of detecting NG in a sample is provided, the method comprising performing an amplifying step comprising contacting the sample with a set of $Piv_{Ng}$ gene primers to produce an amplification product if NG nucleic acid is present in the sample; performing a hybridizing step comprising contacting the amplification product with one or more detectable $Piv_{Ng}$ gene probes; and detecting the presence or absence of the amplification product, wherein the presence of the amplification product is indicative of the presence of NG in the sample and wherein the absence of the amplification product is indicative of the absence of NG in the sample; wherein the set of $Piv_{Ng}$ gene primers comprise a first primer comprising or consisting of a first oligonucleotide sequence of SEQ ID NO: 1, or a complement thereof, and a second primer comprising or consisting of a second oligonucleotide sequence of SEQ ID NO: 2, or a complement thereof and wherein the one or more detectable $Piv_{Ng}$ gene probes comprises or consists of a third oligonucleotide sequence of SEQ ID NO: 3, or a complement thereof. In certain embodiments, the method of detecting NG further comprises contacting the sample with a set of primers and probes for the amplification and detection of the NGDR9 gene sequence that are disclosed in U.S. Pat. No. 7,476,736, and is incorporated herein by reference in its entirety.

In some embodiments the hybridizing step comprises contacting the amplification product with the detectable NG $Piv_{Ng}$ gene probe that is labeled with a donor fluorescent moiety and a corresponding acceptor moiety; and the detecting step comprises detecting the presence or absence of fluorescence resonance energy transfer (FRET) between the donor fluorescent moiety and the acceptor moiety of the probe, wherein the presence or absence of fluorescence is indicative of the presence or absence of NG in the sample. In some embodiments the amplifying and the hybridizing steps are repeated. Herein, the number of repetitions depends, e.g., on the nature of the sample. If the sample is a complex mixture of nucleic acids, more amplifying and hybridizing steps will be required to amplify the target sequence sufficient for detection. In some embodiments, the amplifying and the hybridizing steps are repeated at least about 20 times, but may be repeated as many as at least 25, 30, 40, 50, 60, or even 100 times. Further, detecting the presence or absence of the amplification product may be performed during or after each amplifying and hybridizing step, during or after every other amplifying and hybridizing step, during or after particular amplifying and hybridizing steps or during or after particular amplifying and hybridizing steps, in which—if present—sufficient amplification product for detection is expected. In some embodiments, the amplifying step employs a polymerase enzyme having 5' to 3' nuclease activity. In some embodiments, the donor fluorescent moiety and the corresponding acceptor moiety are within no more than 8-20 nucleotides of each other on the probe. In some embodiments, the acceptor moiety is a quencher. In some embodiments, the oligonucleotides comprise or consist of a sequence of nucleotides selected from SEQ ID NOs: 1-3, or a complement thereof and have 100 or fewer nucleotides, 50 or fewer nucleotides, 40 or fewer nucleotides or 30 or fewer nucleotides. In some embodiments, the first and second NG $Piv_{Ng}$ gene primers and detectable NG $Piv_{Ng}$ gene probes have 40 or fewer nucleotides (e.g. 35 or fewer nucleotides, 30 or fewer nucleotides, etc.). In another embodiment, the present disclosure provides an oligonucleotide that includes a nucleic acid having at least 70% sequence identity (e.g., at least 75%, 80%, 85%, 90% or 95%, etc.) to one of SEQ ID NOs: 1-3, or a complement thereof, which oligonucleotide has 100 or fewer nucleotides. Generally, these oligonucleotides may be primer nucleic acids, probe nucleic acids, or the like in these embodiments. In some embodiments, the oligonucleotides comprise at least one modified nucleotide, e.g., to alter nucleic acid hybridization stability relative to unmodified nucleotides. In some embodiments, the at least one modified nucleotide is selected from the group consisting of a $N^6$-benzyl-dA, a $N^4$-benzyl-dC, a $N^6$-para-tert-butyl-benzyl-dA, and a $N^4$-para-tert-butyl-benzyl-dC. Optionally, the oligonucleotides comprise at least one label and/or at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. In some embodiments, at least one of the first and second target NG gene primers and detectable target NG gene probe comprises at least one modified nucleotide.

In some embodiments, amplification (the amplifying step) can employ a polymerase enzyme having 5' to 3' nuclease activity. Thus, the donor fluorescent moiety and the acceptor moiety, e.g., a quencher, may be within no more than 5 to 20 nucleotides (e.g., 8 or 10) of each other along the length of the probe. In another aspect, the detectable probe includes a nucleic acid sequence that permits secondary structure formation. Such secondary structure formation generally results in spatial proximity between the first and second fluorescent moiety. According to this method, the second fluorescent moiety on the probe can be a quencher.

The present disclosure provides for methods of detecting the presence or absence of Neisseria gonorrhoeae (NG) in a biological sample from an individual. Such methods generally include performing at least one cycling step, which includes an amplifying step and a dye-binding step. Typically, the amplifying step includes contacting the sample with a plurality of pairs of primers designed to target a specific NG gene to produce one or more target NG gene amplification products if the target NG gene nucleic acid molecule is present in the sample, and the dye-binding step includes contacting the target NG gene amplification product with a double-stranded DNA binding dye. In one embodiment, the target NG gene is the NG $Piv_{Ng}$ gene. Such methods also include detecting the presence or absence of binding of the double-stranded DNA binding dye into the amplification product, wherein the presence of binding is indicative of the presence of NG in the sample, and wherein the absence of binding is indicative of the absence of NG in the sample. A representative double-stranded DNA binding dye is ethidium bromide. In addition, such methods also can include determining the melting temperature between the target NG gene amplification product and the double-stranded DNA binding dye, wherein the melting temperature confirms the presence or absence of NG. In certain embodiments, the method of detecting the presence or absence of NG in a biological sample from an individual further comprises performing amplification with a set of primers for the amplification of the NGDR9 gene sequence. In yet another aspect, a kit for detecting the NG $Piv_{Ng}$ gene is provided. The kit can include one or more sets of primers specific for amplification of the NG Piv$_{Ng}$ gene and one or more detectable probes specific for detection of the NG Piv$_{Ng}$ gene amplification products. In one embodiment, the kit further comprises one or more sets of primers and probes for the amplification and detection of the NGDR9 gene sequence.

In particular, the oligonucleotide primers and probes disclosed above in connection with the method according to the invention are suitable to being included in a kit according to the invention. Herein, a kit for detecting the Piv$_{Ng}$ gene of NG is provided comprising a first primer comprising or consisting a first oligonucleotide sequence of SEQ ID NO: 1, or a complement thereof a second primer comprising or consisting a second oligonucleotide sequence of SEQ ID NO: 2, or a complement thereof and a fluorescently detectably labeled probe comprising or consisting a third oligonucleotide sequence of SEQ ID NOs: 3, or a complement thereof, the detectably labeled probe configured to hybridize to an amplicon generated by the first primer and the second primer. In one aspect, the kit can include probes already labeled with donor and corresponding acceptor moiety, e.g., another fluorescent moiety or a dark quencher, or can include fluorophoric moieties for labeling the probes. The kit can also include at least one of nucleoside triphosphates, nucleic acid polymerase, and buffers necessary for the function of the nucleic acid polymerase. The kit can also include a package insert and instructions for using the primers, probes, and fluorophoric moieties to detect the presence or absence of NG in a sample. In some embodiments, the third detectably labeled oligonucleotide sequence comprises a donor fluorescent moiety and a corresponding acceptor moiety. In some embodiments, the acceptor moiety is a quencher. In some embodiments, at least one of the first, second, and third oligonucleotides comprises at least one modified nucleotide. In some embodiments, the at least one modified nucleotide is selected from the group consisting of a N$^6$-benzyl-dA, a N$^4$-benzyl-dC, a N$^6$-para-tert-butyl-benzyl-dA, and a N$^4$-para-tert-butyl-benzyl-dC. In some embodiments, the first, second, and third oligonucleotides have 40 or fewer nucleotides.

In another aspect, compositions are provided comprising a set of oligonucleotide primers for amplifying a target NG gene as disclosed above. In some embodiments, the set of NG Piv$_{Ng}$ gene primers comprises a first primer comprising or consisting of a first oligonucleotide sequence of SEQ ID NO: 1, or a complement thereof, and a second primer comprising or consisting of a second oligonucleotide sequence of SEQ ID NO: 2, or a complement thereof. In certain embodiments the composition further comprises a detectable NG Piv$_{Ng}$ gene probe that comprises or consists of a third oligonucleotide sequence of SEQ ID NO: 3, or a complement thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE FIGURES

FIG. 1 shows PCR growth curves of a real-time PCR experiment generated from NG Piv$_{Ng}$ primers and probe with concentrations of genomic N gonorrhea DNA template from strain #2949 present in 30,000 (NG-2949-Neat), 3,000 (NG-2949-DF10-D1), 300 (NG-2949-DF10-D2), 30 (NG-2949-DF10-D3) and 3 (NG-2949-DF10-D4) genomic equivalent concentrations per PCR reaction (ge/PCR).

DETAILED DESCRIPTION OF THE INVENTION

Diagnosis of NG infection by nucleic acid amplification provides a method for rapidly and accurately detecting the bacterial infection. A real-time assay for detecting NG in a sample is described herein. Primers and probes for detecting NG are provided, as are articles of manufacture or kits containing such primers and probes. The increased sensitivity of real-time PCR for detection of NG compared to other methods, as well as the improved features of real-time PCR including sample containment and real-time detection of the amplified product, make feasible the implementation of this technology for routine diagnosis of NG infections in the clinical laboratory. The present disclosure includes oligonucleotide primers and fluorescent labeled hydrolysis probes that hybridize to a specific gene locus of the NG genome in order to specifically identify NG using TaqMan® amplification and detection technology. Target selection for NG required a comprehensive search of the public sequence database, as well as literature search for NG targets with a potential to discriminate against the nearest neighbors *Neisseria meningitides* (*N. meningitides*) and *Neisseria lactamica* (*N. lactamica*). Multiple targets from the public sequence database were analyzed in the target selection process but many showed cross reactivity with other *Neisseria* species. Furthermore, sequences in the public database are complicated by "bulk" sequence data from multicopy targets. As a result of the analysis, a target NG gene that was chosen was the NG Pilin Inverting protein (Piv$_{Ng}$) gene (GenBank accession number U65994.1, residues 3603-4577).

The disclosed methods may include performing at least one cycling step that includes amplifying one or more portions of the nucleic acid molecule gene target from a sample using one or more pairs of primers. "Primer(s)" as used herein refer to oligonucleotide primers that specifically anneal to the target gene in NG, and initiate DNA synthesis therefrom under appropriate conditions producing the respective amplification products. Each of the discussed primers anneals to a target within or adjacent to the respective target nucleic acid molecule such that at least a portion of each amplification product contains nucleic acid sequence corresponding to the target. The one or more amplification products are produced provided that one or more of the target NG gene nucleic acid is present in the sample, thus the presence of the one or more of target NG gene amplification products is indicative of the presence of NG in the sample. The amplification product should contain the nucleic acid sequences that are complementary to one or more detectable probes for target NG gene. "Probe(s)" as used herein refer to oligonucleotide probes that specifically anneal to nucleic acid sequence encoding the target NG gene. Each cycling step includes an amplification step, a hybridization step, and a detection step, in which the sample is contacted with the one or more detectable probes for detection of the presence or absence of NG in the sample.

As used herein, the term "amplifying" refers to the process of synthesizing nucleic acid molecules that are complementary to one or both strands of a template nucleic acid molecule. Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'—OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except possibly for the intended function—no fundamental difference between a "primer", an "oligonucleotide", or a "probe".

The term "hybridizing" refers to the annealing of one or more probes to an amplification product. Hybridization conditions typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolo-pyrimidine analog, a pseudo-dU, a nitro pyrrole, a nitro indole, 2'-O-methyl Ribo-U, 2'-O-methyl Ribo-C, an N4-ethyl-dC, an $N^6$-methyl-dA, a $N^6$-benzyl-dA, a $N^4$-benzyl-dC, a $N^6$-para-tert-butyl-benzyl-dA, a $N^4$-para-tert-butyl-benzyl-dC, and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference.

Detection of NG

The present disclosure provides methods to detect NG by amplifying, for example, a portion of the NG $Piv_{Ng}$ gene nucleic acid sequence. Nucleic acid sequences of the gene are publicly available (e.g., GenBank Accession No. U65994.1 residues 3603-4577, SEQ ID NO: 4). Specifically, primers and probes to amplify and detect specific NG nucleic acid molecule targets are provided by the embodiments in the present disclosure.

For detection of NG, primers and probes to amplify the NG $Piv_{Ng}$ gene are provided. Nucleic acids other than those exemplified herein can also be used to detect NG in a sample. For example, functional variants can be evaluated for specificity and/or sensitivity by those of skill in the art using routine methods. Representative functional variants can include, e.g., one or more deletions, insertions, and/or substitutions in the target NG gene nucleic acids disclosed herein. More specifically, embodiments of the oligonucleotides each include a nucleic acid with a sequence selected from SEQ ID NOs: 1-3, a substantially identical variant thereof in which the variant has at least, e.g., 80%, 90%, or 95% sequence identity to one of SEQ ID NOs:1-3, or a complement of SEQ ID NOs: 1-3 and the variant.

TABLE I

Piv$_{Ng}$ Primers and Probe

| Oligo Name | SEQ ID NO: | Sequence | Modifications |
|---|---|---|---|
| R6_1483F_TBBC | 1 | CGCAGCATACGCG<t_BB_dC> | t_BB_dC = t-butyl-benzyl dC |
| R6_1483R_TBB | 2 | ATGGCTTTGATGATTTGCG<t_BB_dC> | t_BB_dC = t-butyl-benzyl dC |
| R6_1483_P | 3 | <HEX_Thr>TCATC<BHQ_2>ACGCGGCA AAAGATGAAGAAGCGG<Phos> | HEX_Thr = HEX dye with Thr linker, Q = BHQ2, Phos = phosphate |

In one embodiment, the above described sets of primers and probes are used in order to provide for detection of NG in a biological sample suspected of containing NG. The sets of primers and probes may comprise or consist of the primers and probes specific for the nucleic acid sequence of the NG Piv$_{Ng}$ gene comprising or consisting of the nucleic acid sequences of SEQ ID NOs: 1-3. In another embodiment, the primers and probes for the NG Piv$_{Ng}$ gene comprise or consist of a functionally active variant of any of the primers and probes of SEQ ID NOs: 1-3. In yet another embodiment, the detection of NG in a biological sample further comprises the provision of primers and probes specific for the NGDR9 gene sequence (SEQ ID NO: 5) which are disclosed in U.S. Pat. No. 7,476,736, and is incorporated herein by reference in its entirety.

A functionally active variant of any of the primers and/or probes of SEQ ID NOs: 1-3 may be identified by using the primers and/or probes in the disclosed methods. A functionally active variant of a primer and/or probe of any of the SEQ ID NOs: 1-3 pertains to a primer and/or probe which provide a similar or higher specificity and sensitivity in the described method or kit as compared to the respective sequence of SEQ ID NOs: 1-3.

The variant may, e.g., vary from the sequence of SEQ ID NOs: 1-3 by one or more nucleotide additions, deletions or substitutions such as one or more nucleotide additions, deletions or substitutions at the 5' end and/or the 3' end of the respective sequence of SEQ ID NOs: 1-3. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-deazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the target NG Piv$_{Ng}$ gene can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length). In some embodiments oligonucleotide primers are 40 or fewer nucleotides in length.

In addition to a set of primers, the methods may use one or more probes in order to detect the presence or absence of NG. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a target NG gene nucleic acid. A "probe" can be referred to as a "detection probe" meaning that it detects the target nucleic acid. In some embodiments, the described NG Piv$_{Ng}$ gene probe can be labeled with at least one fluorescent label. In one embodiment, the NG Piv$_{Ng}$ gene probe can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequence comprise or consist of SEQ ID NO: 3.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length. Constructs can include vectors each containing one of NG Piv$_{Ng}$ gene primers and probes nucleic acid molecules. Constructs can be used, for example, as control template nucleic acid molecules. Vectors suitable for use are commercially available and/or produced by recombinant nucleic acid technology methods routine in the art.

NG Piv$_{Ng}$ gene nucleic acid molecules can be obtained, for example, by chemical synthesis, direct cloning from CA, or by PCR amplification.

Constructs suitable for use in the methods typically include, in addition to the NG Piv$_{Ng}$ gene nucleic acid molecules (e.g., a nucleic acid molecule that contains one or more sequences of SEQ ID NOs:1-3), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing target NG gene nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens,* and *Bacillus subtilis.* Eukaryotic hosts include yeasts such as *S. cerevisiae, S. pombe, Pichia pastoris,* mammalian cells such as COS cells or Chinese hamster ovary (CHO) cells, insect cells, and plant cells such as *Arabidopsis thaliana* and *Nicotiana tabacum.* A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described target NG gene nucleic acid sequences. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the described target NG gene nucleic acid molecules. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ nucleic acid such as RNA or DNA (cDNA). The template nucleic acid need not be purified; it may be a minor fraction of a complex mixture, such as nucleic acid contained in human cells. Nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, protozoa viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 15 mM MgCl$_2$, 0.001% (w/v) gelatin, 0.5-1.0 µg protodenatured template DNA, 50 pmoles of each oligonucleotide primer, 2.5 U of Taq polymerase, and 10% DMSO. The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety and a corresponding quencher, which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Cal.), Iowa Black™ (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a fiber optic light source, or other high intensity light source appropriately filtered for excitation in the desired range. As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced there between.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide which contains an amino linker (e.g., C6-amino phosphoramidites available from ABI (Foster City, Calif.) or Glen Research (Sterling, VA)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of NG

The present disclosure provides methods for detecting the presence or absence of NG in a biological or non-biological sample. Methods provided avoid problems of sample contamination, false negatives, and false positives. The methods include performing at least one cycling step that includes amplifying a portion of target nucleic acid molecules from a sample using one or more pairs of primers, and a FRET detecting step. Multiple cycling steps are performed, preferably in a thermocycler. Methods can be performed using the primers and probes to detect the presence of NG, and the detection of the target NG gene indicates the presence of NG in the sample. As described herein, amplification products can be detected using labeled hybridization probes that take advantage of FRET technology. One FRET format utilizes TaqMan® technology to detect the presence or absence of an amplification product, and hence, the presence or absence of CA. TaqMan® technology utilizes one single-stranded hybridization probe labeled with, e.g., one fluorescent dye and one quencher, which may or may not be fluorescent.

When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of NG in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of CA genomes). If amplification of target nucleic acid occurs and an amplification product is produced, the step of hybridizing results in a detectable signal based upon FRET between the members of the pair of probes.

Generally, the presence of FRET indicates the presence of NG in the sample, and the absence of FRET indicates the absence of NG in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of a NG infection.

Representative biological samples that can be used in practicing the methods include, but are not limited to respiratory specimens, fecal specimens, blood specimens, dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release NG nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the probes from the amplification products can confirm the presence or absence of NG in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

It is understood that the embodiments of the present disclosure are not limited by the configuration of one or more commercially available instruments.

Articles of Manufacture/Kits

Embodiments of the present disclosure further provide for articles of manufacture, compositions or kits to detect NG. An article of manufacture can include primers and probes used to detect the target NG gene, together with suitable packaging materials. Compositions can include primers used to amplify the target NG gene. In certain embodiments compositions can also comprise probes for detecting the target NG gene. Representative primers and probes for detection of NG are capable of hybridizing to target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the probes. Examples of suitable FRET donor fluorescent moieties and corresponding acceptor fluorescent moieties are provided above.

Articles of manufacture can also contain a package insert or package label having instructions thereon for using the primers and probes to detect NG in a sample. Articles of manufacture and compositions may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure will be further described in the following examples, which do not limit the scope of the invention described in the claims.

EXAMPLES

The following examples, tables and figures are provided to aid the understanding of the subject matter, the true scope of which is set forth in the appended claims. It is understood that modifications can be made in the procedures set forth without departing from the spirit of the invention.

Example 1

Target selection for NG was the result of a comprehensive search of the public sequence database, as well as a literature search for NG targets with a potential to discriminate against the nearest neighbors, *Neisseria meningitides* and *Neisseria lactamica*. The NG target chosen utilizes the Pilin Inverting protein ($Piv_{NG}$) gene target, and is 7-copies per genome. The $Piv_{NG}$ region contains sequence variants that can affect probe hybridization however these variants did not comprise more than three of the 7-copies in a sequence database review.

Real-time PCR detection of NG were performed using either the Cobas® 4800 system or the Cobas® 6800/8800 systems platforms (Roche Molecular Systems, Inc., Pleasanton, CA). The final concentrations of the amplification reagents are shown below:

TABLE II

PCR Amplification Reagents

| Master Mix Component | Final Conc (50 uL) |
|---|---|
| DMSO | 0-5.4 % |
| NaN3 | 0.027-0.030 % |
| Potassium acetate | 120.0 mM |
| Glycerol | 3.0 % |
| Tween 20 | 0.02 % |
| EDTA | 0-43.9 uM |
| Tricine | 60.0 mM |
| Aptamer | 0.18-0.22 uM |
| UNG Enzyme | 5.0-10.0 U |
| Z05-SP-PZ Polymerase | 30.0-45.0 U |
| dATP | 400.0-521.70 uM |
| dCTP | 400.0-521.70 uM |
| dGTP | 400.0-521.70 uM |
| dUTP | 800.0-1043.40 uM |
| Forward primer oligonucleotides | 0.15-0.50 µM |
| Reverse primer oligonucleotides | 0.15-0.50 µM |
| Probe oligonucleotides | 0.10 µM |
| Manganese Acetate | 3.30-3.80 µM |

The following table shows the typical thermoprofile used for PCR amplification reaction:

TABLE III

PCR Thermoprofile

| Program Name | Target (° C.) | Acquisition Mode | Hold (hh:mm:ss) | Ramp Rate (° C./s) | Cycles | Analysis Mode |
|---|---|---|---|---|---|---|
| Pre-PCR | 50 | None | 00:02:00 | 4.4 | 1 | None |
|  | 94 | None | 00:00:05 | 4.4 |  |  |
|  | 55 | None | 00:02:00 | 2.2 |  |  |
|  | 60 | None | 00:06:00 | 4.4 |  |  |
|  | 65 | None | 00:04:00 | 4.4 |  |  |
| 1st Measurement | 95 | None | 00:00:05 | 4.4 | 5 | Quantification |
|  | 55 | Single | 00:00:30 | 2.2 |  |  |
| 2nd Measurment | 91 | None | 00:00:05 | 4.4 | 45 | Quantification |
|  | 58 | Single | 00:00:25 | 2.2 |  |  |
| Cooling | 40 | None | 00:02:00 | 2.2 | 1 | None |

The Pre-PCR program comprised initial denaturing and incubation at 55° C., 60° C. and 65° C. for reverse transcription of RNA templates. Incubating at three temperatures combines the advantageous effects that at lower temperatures slightly mismatched target sequences (such as genetic variants of an organism) are also transcribed, while at higher temperatures the formation of RNA secondary structures is suppressed, thus leading to a more efficient transcription. PCR cycling was divided into two measurements, wherein both measurements apply a one-step setup (combining annealing and extension). The first 5 cycles at 55° C. allow for an increased inclusivity by pre-amplifying slightly mismatched target sequences, whereas the 45 cycles of the second measurement provide for an increased specificity by using an annealing/extension temperature of 58° C.

The amplification and detection of the $Piv_{NG}$ gene were performed using the conditions described above. The results of an experiment using the oligonucleotide primers of SEQ ID NOs: 1-2 and an oligonucleotide probe of SEQ ID NO: 3 against genomic NG DNA from strain #2949 present at a concentration of 30,000, 3,000 and 300, 30 and 3 genomic equivalent concentrations per PCR reaction (ge/PCR) are shown on FIG. 1. Each assay was performed in duplicate and the showed roughly 3.3-cycles difference in signal between 10-fold dilutions of NG strain #2949.

Example 2

14 strains of NG were used to assess inclusivity of the primer/probe combination of SEQ ID NOs: 1-3. Samples were extracted with a manual Qiagen kit and quantified by nanodrop. In all strains, NG was detected at 3.0e2 ge/PCR (Table IV). The resultant Ct values among each dilution level in the panel are somewhat broad range, which is likely due to inaccuracy of nanodrop readings for nucleic acid quantification.

TABLE IV

NG Inclusivity Data, Ct Values

| NG Strain # | Source | 3.0E4 N = 1 | 3.0E3 Avg, n = 2 | 3.0E2 Avg, n = 2 |
|---|---|---|---|---|
| 351 | Cetus, NRL, Seattle | 24.3 | 33.0 | 36.7 |
| 906 | ATCC via CMCC | 21.5 | 30.0 | 34.1 |
| 2948 | ATCC | 23.6 | 32.7 | 36.1 |
| 2949 | ATCC | 21.8 | 28.2 | 32.3 |
| 3533 | ATCC | 21.0 | 30.2 | 34.0 |
| 3534 | ATCC | 24.6 | 32.6 | 38.4 |
| 3535 | ATCC | 22.9 | 31.8 | 35.6 |
| 3536 | ATCC | 26.7 | 34.4 | 38.4 |
| 3537 | ATCC | 17.2 | 27.0 | 30.5 |
| 3538 | ATCC | 28.0 | 36.1 | 40.3 |
| 6908 | ATCC | 21.1 | 30.1 | 35.5 |
| 1097 | Neisseria Reference Laboratory, Seattle | 23.3 | 31.8 | 35.5 |

TABLE IV-continued

NG Inclusivity Data, Ct Values

| NG Strain # | Source | 3.0E4 N = 1 | 3.0E3 Avg, n = 2 | 3.0E2 Avg, n = 2 |
|---|---|---|---|---|
| 898 | Alameda Co. Public Health Laboratory | 19.0 | 28.0 | 33.6 |
| 1107 | Neisseria Reference Laboratory, Seattle | 20.6 | 29.2 | 33.0 |

Example 3

For NG exclusivity, a panel of 18-strains of commensal Neisseria species were tested (Table V). Samples were purified by a manual Qiagen kit and quantified by nanodrop. No cross reactivity was observed at 3.0 e4 genomic copies/PCR (data not shown).

TABLE V

NG exclusivity panel

| Strain # | Species |
|---|---|
| 6305 | Neisseria flavescens |
| 6318 | N. denitrificans |
| 10231 | N. meningitidis ser D |
| 838 | N. polysaccharea |
| 6339 | N. perflava |
| 836 | N. flava |
| 1927 | N. sicca |
| 6313 | N. lactamica |
| 6322 | N. elongata |
| 2631 | N. subflava |
| 348 | N. meningitidis ser C |
| 349 | N. meningitidis ser Y |
| 6336 | N. mucosa |
| 33926 | N. macacae |
| 577 | sample *577* |
| 839 | N. sicca |
| 10230 | N. weaveri |
| 6317 | N. cinerea |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

INFORMAL SEQUENCE LISTING

SEQ ID NO 1: R6_1483F_TBBC forward primer
CGCAGCATACGCGC

SEQ ID NO 2: R6_1483R_TBB reverse primer
ATGGCTTTGATGATTTGCGC

SEQ ID NO 3: R6_1483_P probe
TCATCACGCGGCAAAAGATGAAGAAGCGG

SEQ ID NO 4: $Piv_{NG}$ gene sequence (GenBank Accession No. U65994.1, residues 3603-4577)
TTACGCCGATTTGTAACGCGATGGATCGTAATCTCCGCCTTTCTTATGTACGTGATAC
GCAATAACGGCGAGTTTACGCATCAATGCTGCGATGATGACTTTTTTAGGCTTCTTC

INFORMAL SEQUENCE LISTING

```
TTTTCTTCCAGCCTTTTGATGAAGTCGGGAAATGCCCTTATCCGGTATGCGACCATG
GCCGGCATAAACAAGACGGCGCGTAATTTCCTGTTGCCAAACTTGGTCAGTTTGCCT
TTTCCCCTTACGCTTGTCCCGGATTCTTTTTGTTGCGGGCTTAAGCCTGCGAACGCTG
CAAATTTGTTTGATGTTTCAAATTTCGAAGATGTTAGATGATGAAACAATACGGCTG
CGGTCATTCTGCCTATTGCCGGTATGGTTTCAAGACGCTTCACGCCTTCCTTGCAGTT
AGGCTTCTCCGTCTGCTCTTTTATCTTCTCCTTTAAAACTTCAAGCTGTTCATTCATGG
CTTTGATGATTTGCGCATATGCTTTGGCCGCTTCTTCATCTTTTGCCGCGTGATGACG
GTTTTTCATTGCCGCGCATTCGCTTTTGATTTGCGCGTATGCTGCGGTCATCCGTAAA
AGCCTGTATTGCTCGTCCGTAGGCTTCTGCCTCTTTACAAGCTCGCTTTCTTTCGCCA
ACCGGCAATACTGCGCTATCAGCTTTGCATCCTGTTTGTCTGTTTTGGTTCGCTTGAA
CCTGCTTTCTGCATACTTGCTTATTTTCAGCGGATTCACTACGTAAACGCTGTAATAC
TGCGCGAAGTAGTCGGCAACTTCTTCATAATAGTTTCCCGTTGCCTCCATGCAGATA
TGCAGATTCTGACATCCCAAGCTTTTCAACCGGTCCGAAAACTGATCTAAACCTTTT
GAATCGTTGTCAAACTTTGCCGAATGCTCCGTTTTGCCGACCATGGCGGATGCGTTA
AAGGTCAGTTTCGATATATCCAATCCTACGGCGTTACGCATGGGATTACCCTT
```

SEQ ID NO 5: NGDR9 gene sequence
```
CAGCCGCATC ATGATGCCGC ACGTCAGGGC TTCGTCTTCCGATACCTTTGCGCCAGACAA
CATCCGGGCG ATGTTTTCTT TTTGCGCTTT TGACCGGGCG GACAGCCGGTTCCGGTCAAC
GTTTCTGACC GTCCCGGCGC GTTTGACGGC GCGTTCCTGC CGCGTTGATTCCTTCGCCGC
GCGTTTGGCG GCAAGCATCT GTTTTGCCGT CGGTTTTGTT GCTACTGTTT GCATTTTGTT
TTCTCGATTT TTTGATGCCG TTCTCTCAAT GCCCAATCAT AAAGCTGTAT CTCTCACGAG
GTCGCCGAAT TTAAATTGAT AGTTCATGTC TTGTTCCATT AATATCAAAC GCAATCTTCA
AACACCTCAA TTACATTTTT TAAATCGCTA ATACCATAAT TTATTACATC CTTTAGAAAT
TCCAAAGAGG TATCCGCTTC GTCTGCTTTA TCCCTAATTT CGTCTATATA ACCCTCTAAC
GATTCAGGCT CTTTTAATGC TTCTTTGCAT AAGTTATCTA TTACCCTTAA TGCGTTTTTT
ACATCTTCCA AATAGCTCAT TTTTTGCTCC TTAACTCAAA ATGGGATGCT GTCGTCAACA
TCTTCTACGG TTTATCTAAT CTGCAAATTC TTCCGCCCTT CAATCTTCGC GCCTGCTACT
TGCCGACCGC TTTCAATCGC TTTTCTGATG GCGGTTTTGT CCGGTTCGGT TTTGACGGCC
TCACGCATAA ATTCGGCGGG GATTTGTGCT TCGTCTAAGATCACGACGGCTTCGGATTTG
CGGAACGAGG CTTTAAAAGT GCCGTC
```

The invention claimed is:

1. A method of detecting *Neisseria gonorrhoeae* (NG) in a sample, the method comprising:

performing an amplifying step comprising contacting the sample with a set of NG PivNg gene primers to produce an amplification product if NG PivNg nucleic acid is present in the sample;

performing a hybridizing step comprising contacting the amplification product with one or more detectable NG PivNg gene probes; and detecting the presence or absence of the amplification product, wherein the presence of the amplification product is indicative of the presence of NG in the sample and wherein the absence of the amplification product is indicative of the absence of NG in the sample;

wherein the set of NG PivNg gene primers comprise a first primer comprising a first oligonucleotide sequence of SEQ ID No: 1, or a complement thereof, and a second primer comprising a second oligonucleotide sequence of SEQ ID No: 2, or a complement thereof; and wherein the one or more detectable NG PivNg gene probes comprises a third oligonucleotide sequence of SEQ ID No: 3, or the complement thereof.

2. The method of claim 1, wherein:

the hybridizing step comprises contacting the amplification product with the detectable NG $Piv_{Ng}$ gene probe that is labeled with a donor fluorescent moiety and a corresponding acceptor moiety; and the detecting step comprises detecting the presence or absence of fluorescence resonance energy transfer (FRET) between the donor fluorescent moiety and the acceptor moiety of the probe, wherein the presence or absence of fluorescence is indicative of the presence or absence of NG in the sample.

3. The method of claim 2, wherein said amplifying step employs a polymerase enzyme having 5' to 3' nuclease activity.

4. The method of claim 2, wherein the donor fluorescent moiety and the corresponding acceptor moiety are within no more than 8-20 nucleotides of each other on the probe.

5. The method of claim 2, wherein the acceptor moiety is a quencher.

6. The method of claim 1, wherein the first and second oligonucleotide each comprises at least one modified nucleotide.

7. The method of claim 6, wherein the at least one modified nucleotide is selected from the group consisting of a $N^6$-benzyl-dA, a $N^4$-benzyl-dC, a $N^6$-para-tert-butyl-benzyl-dA, and a $N^4$-para-tert-butyl-benzyl-dC.

8. The method of claim 1, further comprising the step of contacting the sample with a set of primers and probes for amplification and detection of the NGDR9 gene sequence.

* * * * *

SEQUENCE LISTING

<160> NUMBER OF SEQ ID NOS: 5

<210> SEQ ID NO 1
<211> LENGTH: 14
<212> TYPE: DNA
<213> ORGANISM: Artificial Sequence
<220> FEATURE:
<223> OTHER INFORMATION: R6_1483F_TBBC forward primer
<220> FEATURE:
<221> NAME/KEY: modified_base
<222> LOCATION: (14)..(14)
<223> OTHER INFORMATION: t-butyl-benzyl dC

<400> SEQUENCE: 1
cgcagcatac gcgc                                               14

<210> SEQ ID NO 2
<211> LENGTH: 20
<212> TYPE: DNA
<213> ORGANISM: Artificial Sequence
<220> FEATURE:
<223> OTHER INFORMATION: R6_1483R_TBB reverse primer
<220> FEATURE:
<221> NAME/KEY: modified_base
<222> LOCATION: (20)..(20)
<223> OTHER INFORMATION: t-butyl-benzyl dC

<400> SEQUENCE: 2
atggctttga tgatttgcgc                                         20

<210> SEQ ID NO 3
<211> LENGTH: 29
<212> TYPE: DNA
<213> ORGANISM: Artificial Sequence
<220> FEATURE:

<223> OTHER INFORMATION: R6_1483_P probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' phosphate
<220> FEATURE:
<221> NAME/KEY: misc_feature
<222> LOCATION: (5)..(6)
<223> OTHER INFORMATION: BHQ-2

<400> SEQUENCE: 3

```
tcatcacgcg gcaaaagatg aagaagcgg                              29
```

<210> SEQ ID NO 4
<211> LENGTH: 975
<212> TYPE: DNA
<213> ORGANISM: Neisseria gonorrhoeae

<400> SEQUENCE: 4

```
ttacgccgat ttgtaacgcg atggatcgta atctccgcct ttcttatgta cgtgatacgc    60
aataacggcg agtttacgca tcaatgctgc gatgatgact tttttaggct tcttcttttc   120
ttccagcctt tgatgaagt cgggaaatgc ccttatccgg tatgcgacca tggccggcat    180
aaacaagacg gcgcgtaatt tcctgttgcc aaacttggtc agtttgcctt ttccccttac   240
gcttgtcccg gattcttttt gttgcgggct taagcctgcg aacgctgcaa atttgtttga   300
tgtttcaaat ttcgaagatg ttagatgatg aaacaatacg gctgcggtca ttctgcctat   360
tgccggtatg gtttcaagac gcttcacgcc ttccttgcag ttaggcttct ccgtctgctc   420
ttttatcttc tcctttaaaa cttcaagctg ttcattcatg gctttgatga tttgcgcata   480
tgctttggcc gcttcttcat cttttgccgc gtgatgacgg ttttttcattg ccgcgcattc   540
gcttttgatt tgcgcgtatg ctgcggtcat ccgtaaaagc ctgtattgct cgtccgtagg   600
cttctgcctc tttacaagct cgcttctctt cgccaaccgg caatactgcg ctatcagctt   660
tgcatcctgt ttgtctgttt tggttcgctt gaacctgctt tctgcatact tgcttatttt   720
cagcggattc actacgtaaa cgctgtaata ctgcgcgaag tagtcggcaa cttcttcata   780
atagtttccc gttgcctcca tgcagatatg cagattctga catcccaagc ttttcaaccg   840
gtccgaaaac tgatctaaac cttttgaatc gttgtcaaac tttgccgaat gctccgtttt   900
gccgaccatg gcggatgcgt taaaggtcag tttcgatata ccaatccta cggcgttacg   960
catgggatta ccctt                                                    975
```

<210> SEQ ID NO 5
<211> LENGTH: 806
<212> TYPE: DNA
<213> ORGANISM: Neisseria gonorrhoeae

<400> SEQUENCE: 5

```
cagccgcatc atgatgccgc acgtcagggc ttcgtcttcc gatacctttg cgccagacaa    60
catccgggcg atgttttct tttgcgcttt tgaccgggcg gacagccggt tccggtcaac    120
gtttctgacc gtcccggcgc gtttgacggc gcgttcctgc cgcgttgatt ccttcgccgc   180
gcgtttggcg gcaagcatct gttttgccgt cggttttgtt gctactgttt gcattttgtt   240
ttctcgattt tttgatgccg ttctctcaat gcccaatcat aaagctgtat ctctcacgag   300
gtcgccgaat ttaaattgat agttcatgtc ttgttccatt aatatcaaac gcaatcttca   360
aacacctcaa ttacattttt taaatcgcta ataccataat ttattacatc ctttagaaat   420
```

```
tccaaagagg tatccgcttc gtctgcttta tccctaattt cgtctatata accctctaac    480
gattcaggct cttttaatgc ttctttgcat aagttatcta ttacccttaa tgcgtttttt    540
acatcttcca aatagctcat tttttgctcc ttaactcaaa atgggatgct gtcgtcaaca    600
tcttctacgg tttatctaat ctgcaaattc ttccgccctt caatcttcgc gcctgctact    660
tgccgaccgc tttcaatcgc ttttctgatg gcggttttgt ccggttcggt tttgacggcc    720
tcacgcataa attcggcggg gatttgtgct tcgtctaaga tcacgacggc ttcggatttg    780
cggaacgagg ctttaaaagt gccgtc                                        806
```